(12) United States Patent
Ichinohe et al.

(10) Patent No.: US 6,335,037 B1
(45) Date of Patent: Jan. 1, 2002

(54) COSMETIC COMPRISING SPHERICAL HYDROPHOBIC FINE SILICA PARTICLES

(75) Inventors: Shoji Ichinohe, Takasaki; Muneo Kudo; Akira Yamamoto, both of Annaka, all of (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/526,063

(22) Filed: Mar. 15, 2000

(30) Foreign Application Priority Data

Mar. 17, 1999 (JP) ............................. 11-071598

(51) Int. Cl.⁷ ................................. A61K 9/16
(52) U.S. Cl. .................. 424/490; 424/401; 424/65; 424/489
(58) Field of Search ................. 424/401.65, 489, 424/490

(56) References Cited

U.S. PATENT DOCUMENTS 5,204,088 A * 4/1993 Noebel et al. ............... 424/47

\* cited by examiner

Primary Examiner—Shelley A. Dodson
Assistant Examiner—Konata George
(74) Attorney, Agent, or Firm—Pillsbury Winthrop LLP

(57) ABSTRACT

A cosmetic containing spherical hydrophobic fine silica particles having an average particle diameter of from 0.01 to 5 $\mu$m, having been made more highly hydrophobic, is provided. The spherical hydrophobic fine silica particles have been made hydrophobic on their surfaces by introducing an $R^2SiO_{3/2}$ unit (wherein $R^2$ represents a monovalent hydrocarbon group having 1 to 20 carbon atoms) to the surfaces of hydrophilic fine silica particles having an $SiO_2$ unit, and further have been made more highly hydrophobic on their surfaces by introducing to the surfaces of the hydrophobic fine silica particles first treated an $R^1_3SiO_{1/2}$ unit (wherein $R^1$'s may be the same or different and each represent a monovalent hydrocarbon group having 1 to 6 carbon atoms). The cosmetic containing spherical hydrophobic fine silica particles is a product improved in spreadability and inunctionability.

6 Claims, No Drawings

COSMETIC COMPRISING SPHERICAL HYDROPHOBIC FINE SILICA PARTICLES

BACKGROUND OF THE INVENTION

1. Field of the Invention

This invention relates to cosmetics such as foundations, powders and makeup cosmetics, improved in spreadability and inunctionability.

2. Description of the Prior Art

Cosmetics mixed with powders are conventionally in wide use. These, however, have a poor spreadability and inunctionability especially to the skin, and are sought to be improved in such properties. To cope with such a demand, proposed are an inorganic composite powder surface-treated with a fluorine compound (see Japanese Laid-open Publication (Kokai) No. 6-79163), a powder surface-treated with methylhydrogenpolysiloxane or the like (see Japanese Laid-open Publication (Kokai) No. 5-112430), a hydrophobic powder surface-coated with an acrylic silicone type graft copolymer (see Japanese Laid-open Publication (Kokai) No. 5-339125), an extender pigment comprising potassium titanate coated with a metal oxide (see Japanese Laid-open Publication (Kokai) No. 5-163117), a chitosan powder surface-treated with hydrogenpolysiloxane (see Japanese Laid-open Publication (Kokai) No. 5-86102), a pigment comprising nitride microscopic lamellar substrates coated with a dye/metal oxide (see Japanese Laid-open Publication (Kokai) No. 5-279594), a flaky silica (see Japanese Laid-open Publication (Kokai) No. 6-87720), an ultrafine powder of collagen fibers (see Japanese Laid-open Publication (Kokai) No. 6-107522), a titanium oxide compound having photochromic properties (see Japanese Laid-open Publication (Kokai) No. 5-17152), and a polyamide powder of spherical fine particles (see Japanese Laid-open Publication (Kokai) No. 5-70598). These powders, however, have disadvantages that they not only have an insufficient spreadability to the skin but also have an unstable quality because of a difficulty in manufacture.

A makeup cosmetic is also proposed which has been mixed with polymethylsilasesquioxane as a silicone resin powder (see Japanese Laid-open Publication (Kokai) No. 63-297313). In the case of this cosmetic, it is a little improved in spreadability but has a poor inunctionability.

Silicone rubber powder is also known as a cosmetic powder. This powder has a good softness in itself, but can not improve the spreadability or inunctionability when mixed in cosmetics.

SUMMARY OF THE INVENTION

An object of the present invention is to overcome the disadvantages the prior art has had as stated above, and to provide a cosmetic improved in spreadability and inunctionability.

To achieve the above object, the present invention provides a cosmetic comprising spherical hydrophobic fine silica particles having an average particle diameter of from 0.01 to 5 μm, which are obtained by introducing an $R^2SiO_{3/2}$ unit (wherein $R^2$ represents a monovalent hydrocarbon group having 1 to 20 carbon atoms) to the surfaces of hydrophilic fine silica particles comprising an $SiO_2$ unit to obtain hydrophobic fine silica particles, and introducing an $R^1{}_3SiO_{1/2}$ unit (wherein $R^1$'s may be the same or different and each represent a monovalent hydrocarbon group having 1 to 6 carbon atoms) to the surfaces of the resultant hydrophobic fine silica particles to make the particles more hydrophobic.

DETAILED DESCRIPTION OF THE PREFERRED EMBODIMENTS

Spherical Hydrophobic Fine Silica Particles

The spherical hydrophobic fine silica particles used in the cosmetic of the present invention is a product obtained by introducing an $R^2SiO_{3/2}$ unit (wherein $R^2$ represents a monovalent hydrocarbon group having 1 to 20 carbon atoms) to the surfaces of hydrophilic fine silica particles comprising an $SiO_2$ unit to obtain hydrophobic fine silica particles, and introducing an $R^1{}_3SiO_{1/2}$ unit (wherein $R^1$'s may be the same or different and each represent a monovalent hydrocarbon group having 1 to 6 carbon atoms) to the surfaces of the resultant hydrophobic fine silica particles to make the particles more hydrophobic. From the viewpoint of an improvement in spreadability and inunctionability, the spherical hydrophobic fine silica particles thus obtained must have an average particle diameter within the range of from 0.01 to 5 μm, and preferably from 0.05 to 1 μm. If their average particle diameter is smaller than 0.01 μm, the cosmetic may have a poor spreadability, and, if larger than 5 μm, a poor inunctionability.

The monovalent hydrocarbon group represented by $R^2$ in the $R^2SiO_{3/2}$ unit may include, e.g., alkyl groups such as methyl, ethyl, propyl, butyl, pentyl, hexyl, heptyl, octyl, nonyl and decyl; aryl groups such as phenyl, tolyl and naphthyl; aralkyl groups such as benzyl and phenetyl; alkenyl groups such as vinyl, allyl, hexenyl and cyclohexenyl; and any of these groups at least part of hydrogen atoms of which has been substituted with a halogen atom such as a fluorine atom, as exemplified by a trifluoromethyl group and a heptadecafluorodecyl group. Preferably, $R^2$ includes methyl, ethyl, propyl and butyl groups.

The monovalent hydrocarbon group represented by $R^1$ in the $R^1{}_3SiO_{1/2}$ unit may include, e.g., alkyl groups such as methyl, ethyl, propyl, butyl, pentyl and hexyl. Preferably, $R^1$ includes methyl, ethyl, propyl and butyl groups.

Specifically, the present spherical hydrophobic fine silica particles are produced through the following steps:

the steps of subjecting at least one compound selected from the group consisting of a tetrafunctional silane compound represented by the general formula (I):

$$Si(OR^3)_4 \qquad (I)$$

wherein $R^3$'s may be the same or different and each represent a monovalent hydrocarbon group having 1 to 6 carbon atoms, a partial hydrolysis-condensation product thereof and a mixture of these, to hydrolysis and condensation in a mixed solvent of water and a hydrophilic organic solvent (e.g., methanol or ethanol) containing a basic substance such as ammonia or an organic amine, to prepare a hydrophilic solvent dispersion of hydrophilic fine silica particles, adding water to the resultant dispersion, and thereafter evaporating the hydrophilic organic solvent to convert the dispersion into an aqueous dispersion to hydrolyze the remaining alkoxyl groups completely;

the step of adding to the resultant aqueous dispersion of hydrophilic fine silica particles at least one compound selected from the group consisting of a trifunctional silane compound represented by the general formula (II):

$$R^2Si(OR^4)_3 \qquad (II)$$

wherein $R^2$ represents a monovalent hydrocarbon group having 1 to 20 carbon atoms, and $R^4$'s may be the same or different and each represent a monovalent hydrocarbon group having 1 to 6 carbon atoms, and a partial hydrolysis-condensation product thereof, to treat the hydrophilic fine silica particle surfaces with it to obtain hydrophobic fine silica particles, thus the $R^2SiO_{3/2}$ units being introduced onto the surfaces of the hydrophilic fine silica particles comprising $SiO_2$ units to produce hydrophobic fine silica particles;

the step of converting the resultant aqueous dispersion of hydrophobic fine silica particles into a ketone solvent dispersion by adding a ketone solvent followed by evaporation of water; and the step of adding to the resultant hydrophobic fine silica particle ketone solvent dispersion at least one compound selected from the group consisting of a silazane compound represented by the general formula (III):

$$R^1{}_3SiNHSiR^1{}_3 \qquad (III)$$

wherein $R^1$'s may be the same or different and each represent a monovalent hydrocarbon group having 1 to 6 carbon atoms, and a monofunctional silane compound represented by the general formula (IV):

$$R^1{}_3SiX \qquad (IV)$$

wherein $R^1$'s are as defined in the general formula (III), and X represents a hydroxyl group or a hydrolyzable group, to allow to react with silanol groups remaining on the hydrophobic fine particle surfaces, thereby the silanol groups being trialkylsilylated, i.e., the $R^1{}_3SiO_{1/2}$ units being introduced to the surfaces of the hydrophobic fine silica particles.

The spherical hydrophobic fine silica particles thus finally obtained are particles whose surfaces have been made more highly hydrophobic than the hydrophobic fine silica particles to which the $R^1{}_3SiO_{1/2}$ units have not been introduced. This spherical hydrophobic fine silica particles have no longer any residual reactive groups such as silanol groups and also are highly dispersible and less agglomerative, having a good fluidity, and hence can bring about good results for the object and effect of the present invention.

Examples of the tetrafunctional silane compound represented by the general formula (I) include tetraalkoxysilanes such as tetramethoxysilane, tetraethoxysilane, tetraisopropoxysilane and tetrabutoxysilane. Examples of the partial hydrolysis-condensation product thereof include methyl silicate and ethyl silicate.

Examples of the trifunctional silane compound represented by the general formula (II) include trialkoxysilanes such as methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, butyltrimethoxysilane, butyltriethoxysilane, hexyltrimethoxysilane, trifluoropropyltrimethoxysilane and heptadecafluorodecyltrimethoxysilane.

Examples of the ketone solvent include methyl ethyl ketone, methyl isobutyl ketone and acetyl acetone, and preferably methyl isobutyl ketone.

Examples of the silazane compound represented by the general formula (III) include hexamethyldisilazane. Examples of the monofunctional silane compound represented by the general formula (IV) include monosilanol compounds such as trimethylsilanol and triethylsilanol, monochlorosilanes such as trimethylchlorosilane and triethylchlorosilane, monoalkoxysilanes such as trimethylmethoxysilane and trimethylethoxysilane, monoaminosilanes such as trimethylsilyldimethylamine and trimethylsilyldiethylamine and monoacyloxysilanes such as trimethylacetoxysilane.

Other Components

The cosmetic of the present invention is basically comprised of the spherical hydrophobic fine silica particles described above. Additional powders and other components such as binder oils, surface-active agents, perfumes, antiseptics and solvents which are usually used may optionally be mixed depending on uses such as foundations, creams, powder products and makeup cosmetics.

The additional powders may include, e.g., talc, titanium oxide, mica and zinc oxide. Any of these may be used alone or in combination of two or more types.

The binder oil may include, e. g., liquid paraffin, mineral oils, vegetable oils (such as lanolin and avocado oil) and low-viscosity silicone oil. Any of these may be used alone or in combination of two or more types.

As the surface-active agents, any anionic, cationic, nonionic or amphoteric surface-active agents may be used. Any of these may be used alone or in combination of two or more types.

The solvents may include, e.g., polyethylene glycol, polypropylene glycol, fatty acid esters and higher alcohols. Any of these may be used alone or in combination of two or more types.

The quantities of these optional components to be mixed may vary depending on the types of cosmetics. For example, in the case of foundations, it is suitable for additional powders to be mixed in an amount of from 1 to 1,000 parts by weight; the binder oil, from 1 to 100 parts by weight; the surface-active agent, from 0 to 100 parts by weight; and the solvent, from 1 to 1,000 parts by weight; based on 10 parts by weight of the spherical hydrophobic fine silica particles. In the case of makeup cosmetics such as eye shadow, it is also suitable for additional powders to be mixed in an amount of from 1 to 1,000 parts by weight; the binder oil, from 1 to 100 parts by weight; the surface-active agent, from 0 to 100 parts by weight; and the solvent, from 1 to 1,000 parts by weight; based on 10 parts by weight of the spherical hydrophobic fine silica particles. In the case of powder products such as deodorant powder, it is also suitable for the additional powder to be mixed in an amount of from 1 to 1,000 parts by weight; the binder oil, from 1 to 100 parts by weight; the surface-active agent, from 0 to 100 parts by weight; and the solvent, from 1 to 1,000 parts by weight; based on 10 parts by weight of the spherical hydrophobic fine silica particles.

Production of Cosmetics

The cosmetic of the present invention may be produced by conventionally known processes. For example, the spherical hydrophobic fine silica particles are blended alone or in combination with an additional powder by means of a mixing machine such as a Henschel mixer, a super mixer, a V-blender, an automated mortar or a Nauta mixer. The mixture thus obtained is further mixed with a binder oil, a surface-active agent and so forth having separately dissolved or dispersed in a suitable solvent, by means of a mixing machine such as a ribbon blender or a planetary mixer. Thereafter, this final mixture obtained may optionally be molded by, e.g., press molding to obtain the cosmetic.

Uses

The cosmetic of the present invention is usable as, but not limited to, e.g., foundations; cream of various types; powder products such as deodorant powder, presto powder, face powder and shaving powder; makeup cosmetics such as rouge, eye shadow, mascara and eyeliner; cleaning preparations such as dry shampoo and makeup removers; and sweat controlling preparations of roll-on types or spray types.

EXAMPLES

The present invention will be described below in greater detail by giving Examples and Comparative Examples. The present invention is by no means limited to the following Examples.

Synthesis of Spherical Hydrophobic Fine Silica Particles (1) In a 3-liter glass reaction vessel having a stirrer, a dropping funnel and a thermometer, 623.7 g of methanol, 41.4 g of water and 49.8 g of 28% ammonia water were added and then mixed. The resultant solution was kept at 35° C., and 1,163.7 g of tetramethoxysilane and 418.1 g of 5.4% ammonia water were simultaneously added thereto with stirring the solution, where the former and the latter were added dropwise over a period of 6 hours and 4 hours, respectively. After the tetramethoxysilane had been added dropwise, the mixture was continually stirred for 0.5 hour to carry out hydrolysis, thus a suspension of fine silica particles was obtained. Next, an ester adapter and a condenser were attached to the glass reaction vessel, and the suspension was heated to 60 to 70° C. to distill off 1,132 g of methanol, where 1,200 g of water was added, followed by further heating to 70 to 90° C. to distill off 273 g of methanol, thus an aqueous suspension of fine silica particles was obtained. To this aqueous suspension, 11.6 g of methyltrimethoxysilane (i.e. in a molar ratio thereof to tetramethoxysilane of 0.01) was added dropwise at room temperature over a period of 0.5 hour. After they had been added dropwise, the suspension was also stirred for 12 hours to treat the surfaces of the fine silica particle. To the resultant suspension, 1,440 g of methyl isobutyl ketone was added, followed by heating at 80 to 110° C. for 7 hours to distill off 1,163 g of aqueous methanol. To the resultant suspension, 357.6 g of hexamethyldisilazane was added at room temperature, which was then heated to 120° C. to carry out reaction for 3 hours at this temperature to effect trimethysilylation of the fine silica particles. Then the solvent was distilled off under reduced pressure to obtain 477 g of spherical hydrophobic fine silica particles having an average particle diameter of 0.12 μm (hereinafter "fine silica particles A").

Example 1

Foundation was produced using the following components. In the following, "part(s)" refers to part(s) by weight.

| Component 1: | |
|---|---|
| Talc | 61.0 parts |
| Titanium oxide | 10.0 parts |
| Fine silica particles A | 10.0 parts |
| Component 2: | |
| Stearic acid | 1.5 parts |
| Glycerol monostearate | 0.5 part |
| Myristyl alcohol | 0.5 part |
| Liquid paraffin | 15.0 parts |
| Component 3: | |
| Triethanolamine | 0.5 part |
| Polyethylene glycol | 1.0 part |
| Antisepticin | in an appropriate amount |
| Perfume | in an appropriate amount |

The component 2 was heated to 85° C. to be dissolved uniformly to make up a solution. To this solution, the component 3, having been heated to 82° C., was added with stirring, followed by cooling to room temperature. To the mixture obtained, the component 1 and the perfume, having been mixed by means of a Henschel mixer for 5 minutes, and these were mixed using a ribbon mixer, followed by pulverization to form a uniform product. Next, this product was press-molded into an end product.

Comparative Example 1

Foundation was produced in the same manner as in Example 1 except that the fine silica particles A were replaced with sericite powder.

Example 2

Eye shadow was produced using the following components.

| Component 1: | |
|---|---|
| Mica titanium | 60.0 parts |
| Fine silica particles A | 15.0 parts |
| Zinc laurate | 10.0 parts |
| Component 2: | |
| Liquid paraffin | 10.0 parts |
| Octyl palmitate | 5.0 parts |
| Antioxidant | in an appropriate amount |
| Antiseptic | in an appropriate amount |
| Perfume | in an appropriate amount |

The component 1 was put into a Henschel mixer and mixed for 5 minutes. To the mixture obtained, the component 2, having been mixed and dissolved uniformly, was added, and then mixed using a ribbon mixer, followed by pulverization to form a uniform product. Next, this product was press-molded into an end product.

Comparative Example 2

Eye shadow was produced in the same manner as in Example 2 except that the fine silica particles A were replaced with a silicone rubber powder (KMP-594, available from Shin-Etsu Chemical Co., Ltd.; average particle diameter: 5 μm).

Example 3

Deodorant powder was produced using the following components.

| Component 1: | |
|---|---|
| Zinc oxide | 5.0 parts |
| Tricrosan | 0.1 part |
| Talc | 84.9 parts |
| Fine silica particles A | 5.0 parts |
| Component 2: | |
| Liquid paraffin | 5.0 parts |
| Perfume | in an appropriate amount |

The component 1 was put into a Henschel mixer and mixed for 5 minutes. To the mixture obtained, the component 2, having been mixed and dissolved uniformly, was sprayed, and the spray-coated product obtained was pulverized to obtain an end product.

Comparative Example 3

Deodorant powder was produced in the same manner as in Example 3 except that the fine silica particles A were replaced with a spherical polymethylsilasesquioxane powder (KMP-590, available from Shin-Etsu Chemical Co., Ltd.; average particle diameter: 2 μm).

The cosmetics obtained in Examples and Comparative Examples were used by 10 female trialists to make evaluation tests.

The results of evaluation are as shown in Table 1. Numerals in the table indicate the number of trialists who evaluated "good" in each evaluation item.

TABLE 1

|  | Spreadability | Inunctionability |
| --- | --- | --- |
| Example 1 | 10 | 10 |
| Example 2 | 10 | 9 |
| Example 3 | 10 | 9 |
| Comparative Example 1 | 5 | 6 |
| Comparative Example 2 | 4 | 4 |
| Comparative Example 3 | 6 | 5 |

As described above, the sperical hydrophobic fine silica particles used for the cosmetics of the present invention have small particle diameters and moreover are surface-coated with a silicone compound. Hence, the cosmetics have a good dispersibility, a low agglomerative characteristic and a good fluidity, and are greatly improved in spreadability and inunctionability.

What is claimed is:

1. A cosmetic comprising spherical hydrophobic fine silica particles having an average particle diameter of from 0.01 μm to 5 μm, which are obtained by introducing an $R^2SiO_{3/2}$ unit (wherein $R^2$ represents a monovalent hydrocarbon group having 1 to 20 carbon atoms) to the surfaces of hydrophilic fine silica particles comprising an $SiO_2$ unit to obtain hydrophobic fine silica particles, and introducing an $R^1_3SiO_{1/2}$ unit (wherein $R^1$'s may be the same or different and each represent a monovalent hydrocarbon group having 1 to 6 carbon atoms) to the surfaces of the resultant hydrophobic fine silica particles to make the particles more hydrophobic.

2. The cosmetic of claim 1, wherein said spherical hydrophobic fine silica particles obtained by the two-stage hydrophobic treatment have an average particle diameter of from 0.01 μm to 1 μm.

3. The cosmetic of claim 1, wherein $R^2$ in the $R^2SiO_{3/2}$ unit is methyl, ethyl, propyl or butyl group.

4. The cosmetic of claim 1, wherein $R^1$'s in the $R^1_3SiO_{1/2}$ unit are each methyl, ethyl, propyl or butyl group.

5. The cosmetic of claim 1, which further comprises a component selected from the group consisting of a powder other than the spherical hydrophobic fine silica particles, a binder oil, a surface-active agent, a perfume and a solvent.

6. The cosmetic of claim 1, which is a makeup cosmetic, a cleaning preparation or a sweat controlling preparation.

* * * * *